US007243650B2

(12) United States Patent  
Thornton (10) Patent No.: US 7,243,650 B2  
(45) Date of Patent: Jul. 17, 2007

(54) CUSTOM FITTED MASK CONFIGURED FOR COUPLING TO AN EXTERNAL GAS SUPPLY SYSTEM AND METHOD OF FORMING SAME

(76) Inventor: W. Keith Thornton, 5524 Edlen, Dallas, TX (US) 75220

( * ) Notice: Subject to any disclaimer, the term of this patent is extended or adjusted under 35 U.S.C. 154(b) by 378 days.

(21) Appl. No.: 10/890,547

(22) Filed: Jul. 12, 2004

(65) Prior Publication Data

US 2006/0005837 A1    Jan. 12, 2006

(51) Int. Cl.
*A62B 18/02* (2006.01)
*A62B 18/08* (2006.01)

(52) U.S. Cl. ............... 128/205.25; 128/206.28; 128/206.12; 128/206.14; 128/206.24

(58) Field of Classification Search ........... 128/201.25, 128/205.27, 206.12, 206.13, 206.14, 206.18, 128/206.21, 206.23, 206.24, 206.25, 206.28, 128/207.11; 264/222, 250, 259, 265
See application file for complete search history.

(56) References Cited

U.S. PATENT DOCUMENTS

| 339,334 | A | 4/1886 | Searle | |
|---|---|---|---|---|
| 690,663 | A | 1/1902 | Pratt | 128/204 |
| 746,869 | A | 12/1903 | Moulton | 128/204 |
| 774,446 | A | 11/1904 | Moulton | 128/204 |
| 781,516 | A | 1/1905 | Guthrie, Jr. | 128/204 |
| 885,196 | A | 4/1908 | Steil | 128/204 |

(Continued)

FOREIGN PATENT DOCUMENTS

| AU | 78762/94 | 10/1997 |
|---|---|---|
| AU | 27647/95 | 6/1998 |
| DE | 156627 | 12/1904 |
| DE | 2320501 | 11/1974 |
| DE | 3543931 | 6/1987 |
| DE | 3707952 | 9/1988 |
| DE | 3719009 | 12/1988 |
| DE | 29506512 | 7/1995 |
| DE | 19524534 | 5/1996 |

(Continued)

OTHER PUBLICATIONS

"Donning of the mask" Drager: X-plore 5500. 2006. Drager Safety. Accessed Sep. 14, 2006 <http://www.draeger-usa.com/ST/internet/pdf/US/protection/AnlegePO_X-plore5500_US.pdf>.*

(Continued)

*Primary Examiner*—Justine R. Yu
*Assistant Examiner*—Annette Dixon
(74) *Attorney, Agent, or Firm*—Baker Botts L.L.P.

(57) ABSTRACT

According to one embodiment, a method of forming a custom fitted mask configured for coupling to an external gas supply system includes applying a first sheet of deformable material against a contact portion of a user's face surrounding the user's nostrils while the first sheet is in a deformable state. The first sheet is deformed against the contact portion of the user's face to cause the first sheet to conform substantially optimally to the user's unique facial features. A second sheet of deformable material is configured around a contact portion of a fitting adapted for coupling to the external gas supply system. The second sheet is applied against a contact portion of the first sheet while the second sheet is in a deformable state such that the fitting is positioned between the first and second sheets. The second sheet is deformed against the contact portion of the first sheet with the fitting positioned between the first and second sheets to cause the second sheet to conform substantially optimally to the contact portion of the first sheet. The second sheet is allowed to bond to the contact portion of the first sheet to form the custom fitted mask.

53 Claims, 4 Drawing Sheets

U.S. PATENT DOCUMENTS

| | | | |
|---|---|---|---|
| 893,213 A | 7/1908 | Whiteway | 128/204 |
| 996,783 A | 7/1911 | Moreau | |
| 1,076,534 A | 10/1913 | Wallen | 128/204 |
| 1,146,264 A | 7/1915 | Kelly | 128/204 |
| 1,483,694 A | 2/1924 | Stukey | 128/204 |
| 1,649,664 A | 11/1927 | Carter | 128/204 |
| 1,674,336 A | 6/1928 | King | 128/204 |
| 1,675,202 A | 6/1928 | Warne | |
| 1,679,748 A | 8/1928 | Stratton | |
| 2,171,695 A | 9/1939 | Harper | 32/19 |
| 2,178,128 A | 10/1939 | Waite | 128/136 |
| 2,383,649 A | 8/1945 | Heidbrink | 128/142 |
| 2,424,533 A | 7/1947 | Faires | 128/136 |
| 2,505,028 A | 4/1950 | Boeger | 128/215 |
| 2,521,039 A | 9/1950 | Carpenter | 128/136 |
| 2,521,084 A | 9/1950 | Oberto | 128/141 |
| 2,531,222 A | 11/1950 | Kesling | 32/14 |
| 2,574,623 A | 11/1951 | Clyde | 128/136 |
| 2,590,118 A | 3/1952 | Oddo, Jr. | 128/136 |
| 2,627,268 A | 2/1953 | Leppich | 128/136 |
| 2,671,446 A | 3/1954 | Mann | 128/163 |
| 2,712,160 A | 7/1955 | Sterczek | 18/55.05 |
| 2,833,278 A | 5/1958 | Ross | 128/136 |
| 2,867,212 A | 1/1959 | Nunn, Jr. | 128/136 |
| 2,882,893 A | 4/1959 | Godfroy | 128/136 |
| 2,917,045 A | 12/1959 | Schildknecht et al. | 128/141 |
| 2,977,636 A | 4/1961 | McGuire | 18/58.7 |
| 3,037,501 A | 6/1962 | Miller | 128/141 |
| 3,064,354 A | 11/1962 | Pos | 32/19 |
| 3,107,668 A | 10/1963 | Thompson | 128/136 |
| 3,124,129 A | 3/1964 | Grossberg | 128/136 |
| 3,132,647 A | 5/1964 | Corniello | 128/136 |
| 3,219,033 A | 11/1965 | Wallshein | 128/136 |
| 3,277,892 A | 10/1966 | Tepper | 128/172.1 |
| 3,312,216 A | 4/1967 | Wallshein | 128/136 |
| 3,321,832 A | 5/1967 | Weisberg | 32/32 |
| 3,330,274 A * | 7/1967 | Bennett | 128/206.26 |
| 3,434,470 A | 3/1969 | Strickland | 128/136 |
| 3,457,916 A | 7/1969 | Wolicki | 128/136 |
| 3,513,838 A | 5/1970 | Foderick et al. | 128/136 |
| 3,522,805 A | 8/1970 | Wallshein | 128/136 |
| 3,658,058 A | 4/1972 | Neidhart et al. | 128/147 |
| 3,690,004 A | 9/1972 | Frush | 32/17 |
| 3,695,265 A | 10/1972 | Brevik | 128/146.2 |
| 3,845,768 A | 11/1974 | Garrahan | |
| 3,854,208 A | 12/1974 | Arant | 32/19 |
| 3,864,832 A | 2/1975 | Carlson | 128/136 |
| 3,871,370 A | 3/1975 | McDonald | 128/136 |
| 3,882,601 A | 5/1975 | Jahn | 32/17 |
| 3,884,226 A | 5/1975 | Tepper | 128/136 |
| 4,016,650 A | 4/1977 | Leusner et al. | 32/17 |
| 4,026,024 A | 5/1977 | Tradowsky | 32/19 |
| 4,114,614 A | 9/1978 | Kesling | 128/136 |
| 4,169,473 A | 10/1979 | Samelson | 128/136 |
| 4,182,312 A | 1/1980 | Mushabac | 433/68 |
| 4,227,877 A | 10/1980 | Tureaud et al. | 433/37 |
| 4,233,972 A | 11/1980 | Hauff et al. | 128/205 |
| 4,289,127 A | 9/1981 | Nelson | 128/207.14 |
| 4,294,243 A | 10/1981 | Ernsting et al. | 128/201.18 |
| 4,304,227 A | 12/1981 | Samelson | 128/136 |
| 4,345,592 A | 8/1982 | Giorgini et al. | 128/204 |
| 4,345,593 A | 8/1982 | Sullivan | 128/204 |
| 4,376,628 A | 3/1983 | Aardse | 433/80 |
| 4,382,783 A | 5/1983 | Rosenberg | 433/19 |
| 4,392,490 A | 7/1983 | Mattingly et al. | 128/202 |
| 4,397,701 A | 8/1983 | Johnson et al. | 156/62 |
| 4,433,956 A | 2/1984 | Witzig | 433/7 |
| 4,439,147 A | 3/1984 | Magill et al. | 433/3 |
| 4,439,149 A | 3/1984 | Devincenzo | 433/6 |
| 4,454,090 A | 6/1984 | Saumell | 264/154 |
| 4,470,413 A | 9/1984 | Warncke | 128/201.18 |
| 4,495,945 A | 1/1985 | Liegner | 128/200.26 |
| 4,505,672 A | 3/1985 | Kurz | 433/6 |
| 4,530,662 A | 7/1985 | Andersson et al. | 433/37 |
| 4,553,549 A | 11/1985 | Pope et al. | 128/421 |
| 4,568,280 A | 2/1986 | Ahlin | 433/6 |
| 4,569,342 A | 2/1986 | von Nostitz | 128/136 |
| 4,593,686 A | 6/1986 | Lloyd et al. | 128/136 |
| 4,602,905 A | 7/1986 | O'Keefe, III | 433/41 |
| 4,639,220 A | 1/1987 | Nara et al. | 433/69 |
| 4,655,213 A | 4/1987 | Rapoport et al. | 128/205.25 |
| 4,668,188 A | 5/1987 | Wolfenson et al. | 433/37 |
| 4,669,459 A | 6/1987 | Spiewak et al. | 128/136 |
| 4,676,240 A | 6/1987 | Gardy | 128/207.14 |
| 4,706,683 A | 11/1987 | Chilton et al. | 128/654 |
| 4,715,368 A | 12/1987 | George | 128/136 |
| 4,773,853 A | 9/1988 | Kussick | 433/6 |
| 4,784,123 A * | 11/1988 | Robeson | 602/8 |
| 4,799,500 A | 1/1989 | Newbury | 128/859 |
| 4,858,606 A | 8/1989 | Hamlin | 128/204 |
| 4,862,903 A | 9/1989 | Campbell | 128/861 |
| 4,870,962 A | 10/1989 | Sitnik | 128/205 |
| 4,886,056 A * | 12/1989 | Simpson | 128/201.25 |
| 4,892,478 A | 1/1990 | Tateosian et al. | 433/6 |
| 4,901,737 A | 2/1990 | Toone | 128/848 |
| 4,906,234 A | 3/1990 | Voychehovski | 604/79 |
| 4,919,128 A | 4/1990 | Kopala et al. | 128/207.18 |
| 4,932,867 A | 6/1990 | Ueno | 433/69 |
| 4,941,212 A | 7/1990 | Liff | 2/206 |
| 4,955,393 A | 9/1990 | Adell | 128/859 |
| 4,957,124 A | 9/1990 | Mooney | 132/200 |
| RE33,442 E | 11/1990 | George | 128/860 |
| 5,003,994 A | 4/1991 | Cook | 128/848 |
| 5,011,407 A | 4/1991 | Pelerin | 433/48 |
| 5,018,533 A | 5/1991 | Hawkins | 128/848 |
| 5,026,278 A | 6/1991 | Oxman et al. | 433/41 |
| 5,028,232 A | 7/1991 | Snow | 433/24 |
| 5,040,976 A | 8/1991 | Ubel, III et al. | 433/41 |
| 5,042,478 A | 8/1991 | Kopala et al. | 128/207.18 |
| 5,042,506 A | 8/1991 | Liberati | 128/848 |
| 5,046,512 A | 9/1991 | Murchie | 128/848 |
| 5,052,409 A | 10/1991 | Tepper | 128/859 |
| 5,055,039 A | 10/1991 | Abbatte et al. | 433/24 |
| 5,056,534 A | 10/1991 | Wright | 128/848 |
| 5,062,421 A * | 11/1991 | Burns et al. | 128/205.27 |
| 5,064,371 A | 11/1991 | Smeltzer | 433/37 |
| 5,065,756 A | 11/1991 | Rapoport | 128/204 |
| 5,066,231 A | 11/1991 | Oxman et al. | 433/214 |
| 5,078,600 A | 1/1992 | Austin | 433/73 |
| 5,092,346 A | 3/1992 | Hays et al. | 128/848 |
| 5,103,838 A | 4/1992 | Yousif | 128/859 |
| 5,112,225 A | 5/1992 | Diesso | 433/48 |
| 5,117,816 A | 6/1992 | Shapiro et al. | 128/200.24 |
| 5,154,184 A | 10/1992 | Alvarez | 128/848 |
| 5,154,609 A | 10/1992 | George | 433/68 |
| 5,183,057 A | 2/1993 | Syrop et al. | 128/845 |
| 5,188,529 A | 2/1993 | Lüth | 433/68 |
| 5,190,457 A | 3/1993 | Schreinemakers | 433/214 |
| 5,193,532 A | 3/1993 | Moa et al. | 128/204 |
| 5,213,498 A | 5/1993 | Pelerin | 433/37 |
| 5,233,978 A | 8/1993 | Callaway | 128/205.25 |
| 5,243,971 A | 9/1993 | Sullivan et al. | 128/205 |
| 5,245,995 A | 9/1993 | Sullivan et al. | 128/204 |
| 5,267,557 A | 12/1993 | Her-Mou | 128/206.21 |
| 5,267,862 A | 12/1993 | Parker | 433/215 |
| 5,277,202 A | 1/1994 | Hays | 128/848 |
| 5,284,161 A | 2/1994 | Karell | 128/848 |
| 5,313,960 A | 5/1994 | Tomasi | 128/848 |
| 5,316,020 A | 5/1994 | Truffer | 128/848 |
| 5,320,533 A | 6/1994 | Lee | 433/218 |
| 5,365,945 A | 11/1994 | Halstrom | 128/848 |
| 5,370,533 A | 12/1994 | Bushnell | 433/36 |
| 5,373,859 A | 12/1994 | Forney | 128/846 |
| 5,392,773 A | 2/1995 | Bertrand | 128/206.11 |

| | | | |
|---|---|---|---|
| 5,409,017 A | 4/1995 | Lowe | 128/848 |
| 5,415,544 A | 5/1995 | Oxman et al. | 433/48 |
| 5,427,117 A | 6/1995 | Thornton | 128/848 |
| 5,456,264 A | 10/1995 | Series et al. | 128/725 |
| 5,458,137 A | 10/1995 | Axe et al. | 128/204 |
| 5,477,850 A | 12/1995 | Zegler et al. | 128/202 |
| 5,503,146 A | 4/1996 | Froehlich et al. | 128/204 |
| 5,503,552 A | 4/1996 | Diesso | 433/37 |
| 5,517,983 A | 5/1996 | Deighan et al. | 128/204 |
| 5,537,994 A | 7/1996 | Thornton | 128/205 |
| 5,537,999 A | 7/1996 | Dearman et al. | 128/205 |
| 5,538,000 A | 7/1996 | Rudolph | 128/205 |
| 5,538,014 A | 7/1996 | Wilson et al. | 128/863 |
| 5,540,223 A | 7/1996 | Starr et al. | 128/205.25 |
| 5,551,419 A | 9/1996 | Froehlich et al. | 128/204 |
| 5,551,872 A | 9/1996 | Mena | 433/37 |
| 5,558,090 A | 9/1996 | James | 128/207.18 |
| RE35,339 E | 10/1996 | Rapoport | 128/204 |
| 5,560,354 A | 10/1996 | Berthon-Jones et al. | 128/205 |
| 5,562,449 A | 10/1996 | Jacobs et al. | 433/215 |
| 5,566,683 A | 10/1996 | Thornton | 128/848 |
| 5,582,517 A | 12/1996 | Adell | 433/6 |
| 5,592,935 A | 1/1997 | Elstran et al. | 128/205 |
| 5,611,485 A | 3/1997 | Davis | 239/8 |
| 5,657,751 A | 8/1997 | Karr, Jr. | 128/205 |
| 5,657,752 A | 8/1997 | Landis et al. | 128/207 |
| 5,662,101 A | 9/1997 | Ogden et al. | 128/205.25 |
| 5,676,133 A | 10/1997 | Hickle et al. | 128/205 |
| 5,678,567 A | 10/1997 | Thornton et al. | 128/848 |
| 5,687,715 A | 11/1997 | Landis et al. | 128/207.18 |
| 5,713,349 A | 2/1998 | Keaney | 128/204 |
| 5,718,244 A | 2/1998 | Thornton | 128/864 |
| 5,718,500 A | 2/1998 | Vinci guerra et al. | 2/431 |
| 5,720,280 A | 2/1998 | Elstran et al. | 128/205 |
| 5,720,302 A | 2/1998 | Belfer | 128/201.26 |
| 5,724,965 A | 3/1998 | Handke et al. | 128/207.13 |
| 5,746,201 A | 5/1998 | Kidd | 128/206 |
| 5,752,510 A | 5/1998 | Goldstein | 128/207 |
| 5,755,219 A | 5/1998 | Thornton | 128/201 |
| 5,807,100 A | 9/1998 | Thornton | 433/48 |
| 5,810,749 A | 9/1998 | Maas | 602/6 |
| 5,829,441 A | 11/1998 | Kidd et al. | 128/848 |
| 5,832,918 A | 11/1998 | Pantino | 128/205.25 |
| 5,846,082 A | 12/1998 | Thornton | 433/215 |
| 5,887,587 A | 3/1999 | Groenke | 128/207 |
| 5,891,372 A | 4/1999 | Besset et al. | 264/46.5 |
| 5,954,048 A | 9/1999 | Thornton | 128/201 |
| 5,983,892 A | 11/1999 | Thornton | 128/201 |
| 5,988,166 A | 11/1999 | Hayek | 128/205 |
| 6,012,455 A | 1/2000 | Goldstein | 128/207 |
| 6,083,442 A | 7/2000 | Gabilly | 264/163 |
| 6,119,694 A | 9/2000 | Correa et al. | 128/207.13 |
| 6,155,262 A | 12/2000 | Thornton et al. | 128/859 |
| 6,155,267 A | 12/2000 | Thornton | 128/859 |
| 6,209,542 B1 | 4/2001 | Thornton | 128/206.29 |
| 6,247,926 B1 | 6/2001 | Thornton | 433/48 |
| 6,263,871 B1 | 7/2001 | Brown et al. | 128/200.29 |
| D448,473 S | 9/2001 | Barnett et al. | D24/110.1 |
| 6,305,376 B1 | 10/2001 | Thornton | 128/848 |
| 6,325,064 B1 | 12/2001 | Thornton | 128/204.18 |
| 6,374,824 B1 | 4/2002 | Thornton | 128/201.26 |
| 6,405,729 B1 | 6/2002 | Thornton | 128/848 |
| 6,412,488 B1 | 7/2002 | Barnett et al. | 128/207.13 |
| 6,464,924 B1 * | 10/2002 | Thornton | 264/331.12 |
| 6,494,206 B1 | 12/2002 | Bergamaschi et al. | 128/206.24 |
| 6,516,805 B1 | 2/2003 | Thornton | 128/848 |
| 6,571,798 B1 | 6/2003 | Thornton | 128/206.21 |
| 6,645,413 B2 | 11/2003 | Jacobs | 264/222 |
| 6,675,802 B1 | 1/2004 | Thornton | 128/206.29 |
| 6,857,428 B2 * | 2/2005 | Thornton | 128/206.21 |
| 6,877,513 B2 | 4/2005 | Scarberry et al. | 128/848 |
| 7,077,138 B2 * | 7/2006 | Bateman et al. | 128/206.14 |
| 2002/0000230 A1 | 1/2002 | Gaskell | 128/848 |
| 2004/0237965 A1 | 12/2004 | Bibi et al. | 128/206.29 |
| 2005/0016544 A1 | 1/2005 | Thornton | 128/207.18 |

FOREIGN PATENT DOCUMENTS

| | | |
|---|---|---|
| EP | 0312368 | 4/1989 |
| EP | 0359135 | 3/1990 |
| FR | 2658725 | 2/1990 |
| GB | 1569129 | 6/1980 |
| WO | WO 91/12777 | 9/1991 |
| WO | WO 98/20924 | 5/1998 |
| WO | WO 98/26736 | 6/1998 |
| WO | WO 98/41677 | 10/1998 |
| WO | WO 98/46177 | 10/1998 |

OTHER PUBLICATIONS

Mayo Clinic Health Letter, vol. 13, No. 7, "Snoring."
Photocopies of 2-piece dental device manufactured by Currie-Gibson Dental Laboratory, Inc. prior to Apr. 13, 1993.
Farrar & McCarty, "A Clinical Outline of Temporomandibular Joint Diagnosis and Treatment," Normandie Study Group for TMJ Dysfunction, 3 pages.
Professional Positioners brochure, "Dedicated to Excellence," 4 pages.
Great Lakes Orthodontics, Ltd., "Nocturnal Airway Patency Appliance™ (NAPA)," General Instructions, 2 pages.
Schmidt-Nowara, et al., "Oral Appliances for the Treatment of Snoring and Obstructive Sleep Apnea: A Review," Sleep, 18(6):501-510.
George, "Treatment of Snoring and Obstructive Sleep Apnea with a Dental Device," General Dentistry, 5 pages.
Database WOI, Section PQ, Week 9039, Derwent Publications, Ltd., London, GB XP-002116355—Abstract "Surgical Mouth Air Duct."
CPAP/PRO® . . . Introducing a New Cmfort Level for CPAP Users!! brochure, 2 pages.
PCT International Search Report, PCT/US97/08708, 4 pages.
PCT, International Searching Authority, PCT/US03/13705, 5 pages, Oct. 10, 2003.
W. Keith Thornton, "Device and Mask for Improving a User's Breathing," U.S. Appl. No. 10/428,904, pending, filed May 1, 2003.
W. Keith Thornton, "Custom Fitted Mask and Method of Forming Same," U.S. Appl. No. 10/280,803, pending, filed Oct. 24, 2003.
Thornton, "Multi-Chamber Mask and Method of Forming the Same," U.S. Appl. No. 11/428,933, Filed Jul. 6, 2006, 23 pages.
Great Lakes Orthodontics, Ltd.; "Nocturnal Airway Patency Applicance;" brochure, 2 pages.

* cited by examiner

CUSTOM FITTED MASK CONFIGURED FOR COUPLING TO AN EXTERNAL GAS SUPPLY SYSTEM AND METHOD OF FORMING SAME

TECHNICAL FIELD

This invention relates generally to masks for use in medical or other clinical applications, and more particularly to a custom fitted mask configured for coupling to an external gas supply system and method of forming same.

BACKGROUND

Many people experience breathing problems on a recurring basis, which often results in sleep disordered breathing (i.e., difficulty sleeping, snoring, or other more serious conditions such as obstructive sleep apnea). As technology advances, people with such breathing problems demand increased performance and comfort. Previous devices for improving a user's breathing have included custom fitted masks that help deliver air or another suitable gas to the user's nose at positive pressure to help force open the user's breathing passage and thus improve the user's breathing. However, previous masks may be relatively expensive due to the expertise often required to design, manufacture, and fit the masks to each particular user. Furthermore, previous masks have often been fitted to the user's unique bone structure and facial features rather poorly, if at all. As a result, previous masks have often failed to adequately prevent leakage from around the perimeter of the mask, have caused discomfort for users, and have been relatively ineffective in treating breathing problems such as sleep disordered breathing.

SUMMARY OF THE INVENTION

According to the present invention, problems and disadvantages associated with previous masks and methods for forming them may be reduced or eliminated.

According to one embodiment, a method of forming a custom fitted mask configured for coupling to an external gas supply system includes applying a first sheet of deformable material against a user's face surrounding the user's nostrils while the first sheet is in a deformable state. The first sheet is deformed against the user's face to cause the first sheet to conform substantially optimally to the user's unique facial features. A second sheet of deformable material is configured around a fitting adapted for coupling to the external gas supply system. A contact portion of the second sheet is applied against a contact portion of the first sheet while the second sheet is in a deformable state such that the fitting is positioned between the first and second sheets. The contact portion of the second sheet is deformed against the contact portion of the first sheet with the fitting positioned between the first and second sheets to cause the contact portion of the second sheet to conform substantially optimally to the contact portion of the first sheet. The contact portion of the second sheet is allowed to bond to the contact portion of the first sheet to form the custom fitted mask configured for coupling to the external gas supply system.

According to another embodiment, a method of configuring a mask for coupling to an external gas supply system includes configuring a sheet of deformable material around a fitting adapted for coupling to the external gas supply system. A contact portion of the sheet of deformable material is applied against a contact portion of the mask while the sheet is in a deformable state. The contact portion of the sheet is deformed against the contact portion of the mask with the fitting positioned between the sheet and the mask to cause the contact portion of the sheet to conform substantially optimally to the contact portion of the mask. The contact portion of the sheet is allowed to bond to the contact portion of the mask.

According to another embodiment, a custom fitted mask configured for coupling to an external gas supply system includes a first sheet of deformable material that has been deformed against a user's face surrounding the user's nostrils while the first sheet is in a deformable state to conform substantially optimally to the user's unique facial features. A fitting is adapted for coupling to the external gas supply system. A second sheet of deformable material is configured around the fitting, the second sheet having been applied against the fitting while the second sheet is in a deformable state such that the fitting is positioned between the first and second sheets. A contact portion of the second sheet is conformed substantially optimally to the contact portion of the first sheet and bonded to the contact portion of the first sheet.

According to another embodiment, a mask configured for coupling to an external gas supply system includes a mask adapted to be positioned on a user's face. A fitting is adapted for coupling to the mask and to the external gas supply system. A sheet of deformable material is configured around the fitting, the sheet having been applied against the fitting while the sheet is in a deformable state such that the fitting is positioned between the mask and the sheet. A contact portion of the sheet is conformed substantially optimally to a contact portion of the mask and bonded to the contact portion of the mask.

Certain embodiments of the present invention may provide one or more technical advantages. For example, in certain embodiments, a custom fitted mask may be formed and fitted to a particular user relatively quickly and easily, with little expertise required on the part of the clinical professional who is producing the mask, typically resulting in improved efficiency for the clinical professional and reduced cost to the user. In certain embodiments, a custom fitted mask may be formed and fitted to a particular user so as to conform substantially optimally to the user's unique facial features. In certain embodiments, the custom fitted mask substantially prevents externally supplied gas from escaping between the first sheet and the user's face and from between the first and second sheets. In certain embodiments, the custom fitted mask may provide improved fit, reduced leakage, increased comfort, and better performance, whether in treating breathing problems such as sleep disordered breathing or for any other suitable purpose for which the custom fitted mask is used. A custom fitted or other mask may also be configured for coupling to an external gas supply system relatively quickly and easily, with similar benefits. In certain embodiments, a custom fitted or other mask may be configured, using an appropriate fitting, for coupling to virtually any external gas supply system. In certain embodiments, externally supplied gas is substantially prevented from escaping between a deformable sheet and the underlying custom fitted or other mask. Certain embodiments of the present invention may provide some, all, or more of these advantages. Certain embodiments may provide one or more other advantages, one or more of which may be readily apparent to those skilled in the art from the figures, descriptions, and claims included herein.

BRIEF DESCRIPTION OF THE DRAWINGS

For a more complete understanding of the present invention and advantages thereof, reference is made to the following descriptions taken in conjunction with the accompanying drawings, in which like reference numbers indicate like features and wherein.

DESCRIPTION OF EXAMPLE EMBODIMENTS

Figure 1:
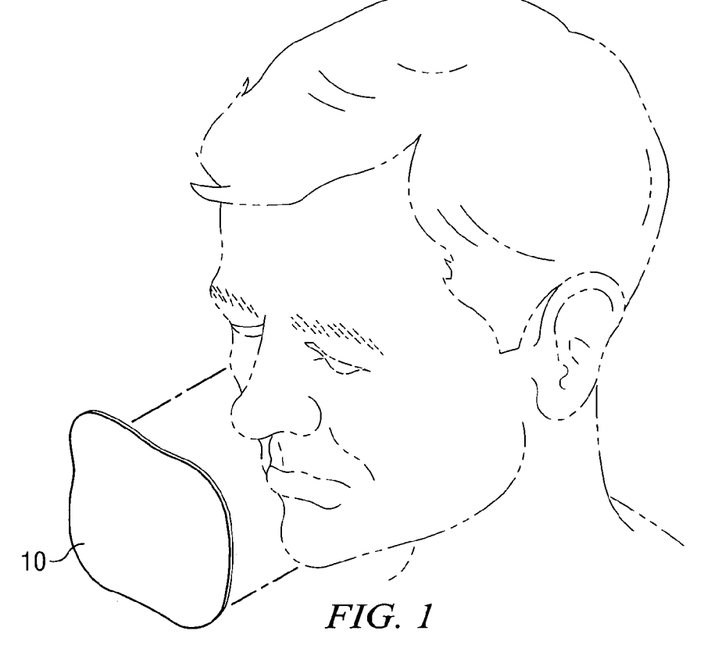
FIG. 1 illustrates an example first sheet of deformable material for forming a custom fitted mask.

FIG. 1 illustrates an example first sheet 10 of deformable material for forming a custom fitted mask. In certain embodiments, first sheet 10 begins as a deformable mask blank made of a suitable deformable material. For example, first sheet 10 may include a suitable thermoplastic polymer and suitable fillers, stabilizers, coloring agents, antioxidants, antimicrobial agents, or other materials. As another example, first sheet 10 may include a light curing material such as the material sold under the name TRIAD by DENTSPLY INTERNATIONAL INC. Such materials are well known in various other contexts to those skilled in the art.

In a more particular embodiment, first sheet 10 may include, possibly in addition to one or more other materials, one or more of the polycaprolactone polymers or other aliphatic polyesters that are described in U.S. Pat. Nos. 4,784,123 and 5,112,225 and product literature of UNION CARBIDE CORPORATION. One or more polycaprolactone polymers may have the formula:

(1)

where R is an aliphatic hydrocarbon and n may range between approximately 300 to approximately 650. The TONE polycaprolactone polymers are described in U.S. Pat. Nos. 4,784,123 and 5,112,225 and product literature of UNION CARBIDE CORPORATION as including homopolymers, block copolymers, graft copolymers, or other polymers containing epsilon-caprolactone. Polymerization may be initiated using a diol, for example and without limitation, ethylene glycol, diethylene glycol, neopentyl glycol, butane diol, hexane diol, or any other appropriate diol. The diol may have the formula:

(2)

where R is an aliphatic hydrocarbon. Where first sheet 10 includes one or more polycaprolactone polymers, any suitable polycaprolactone polymer or polymers may be used. In general, polycaprolactone polymers may display desirable dimensional stability and thermoplasticity during cooling, biocompatibility, and other characteristics making them suitable for use in forming first sheet 10 as described herein.

In certain embodiments, first sheet 10 may include a thin sheet of deformable material that is already contoured in the shape of a portion of a generic user's face, including at least the portion of the generic user's nose surrounding the generic user's nostrils. For example, first sheet 10 may be sized and shaped such that it will cover only the soft cartilaginous portions of the generic user's nose and portions of the generic user's face to the sides of and below the soft cartilaginous portions of the generic user's nose, but will not cover the hard bony portions of the generic user's nose generally above the soft cartilaginous portions of the generic user's nose. In certain other embodiments, first sheet 10 may include a thin sheet of deformable material that is substantially flat except for a depression sufficient to accommodate a generic user's nose, including at least the portion of the generic user's nose surrounding the user's nostrils. In certain other embodiments, first sheet 10 may include a thin sheet of deformable material that is substantially flat over its entire surface and does not include any depressions.

Thin sheets of an appropriate deformable material may be obtained, for example, from CHESAPEAKE MEDICAL PRODUCTS, INC. First sheet 10 may include pre-formed holes positioned according to the position of a generic user's nostrils. Alternatively, one or more holes may be cut from first sheet 10 after first sheet 10 has been positioned on the user's face such that a more precise alignment of the holes with the user's nostrils may be achieved. Particularly where first sheet 10 is formed to include a depression for receiving the user's nose, first sheet 10 may be formed using an injection molding process (i.e., deformable material is placed into an injection molding machine while in a liquid state), using a pressing process (i.e., deformable material is placed into a press while in a deformable state), or using any other suitable technique. First sheet 10 may be sized for various classes of generic users, for example, large for men, medium for women, and small for children. In certain embodiments, many first sheets 10 may be mass produced quickly, inexpensively, and with high quality and uniformity. First sheet 10 may include any other suitable features.

Figure 2:
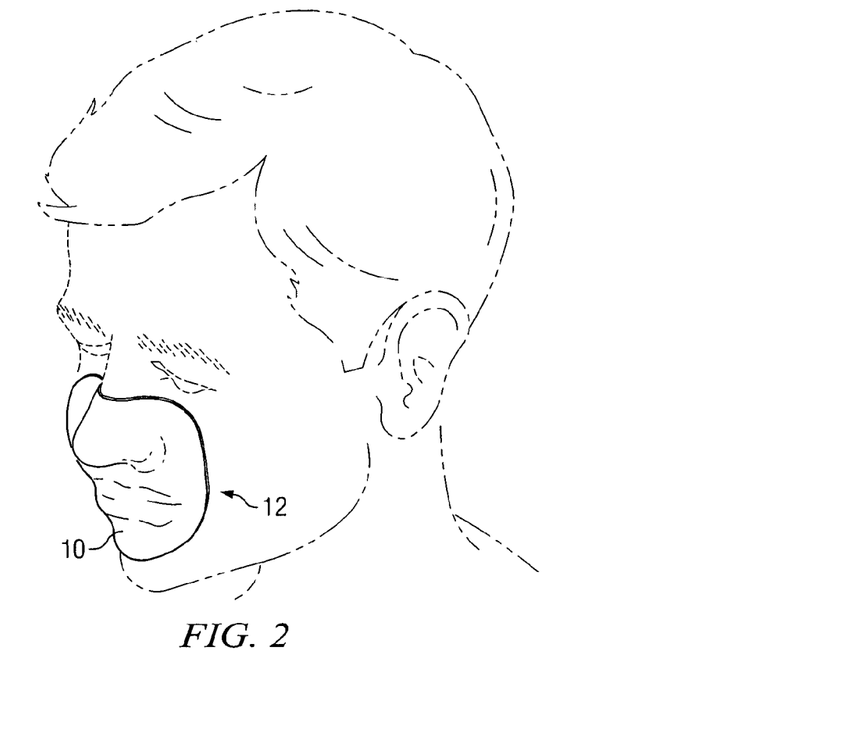
FIG. 2 illustrates an example first sheet of deformable material deformed against a user's face to form a custom fitted mask.

FIG. 2 illustrates an example first sheet 10 of deformable material deformed against a user's face to form a custom fitted mask 12. To form and fit mask 12 for a particular user, first sheet 10 is placed in a deformable state. For example, where the deformable material of first sheet 10 includes one or more polycaprolactone polymers, first sheet 10 may be heated in a microwave oven, in water or other non-solvent neutral liquid, or in any other suitable manner to between approximately 140° F. and approximately 180° F. so as to place first sheet 10 in a deformable state. While in a deformable state, sheet 10 is brought in contact with the user's face, including at least a portion of the user's nose surrounding the user's nostrils. First sheet 10 is then pressed against or otherwise allowed to conform to the user's unique bone structure and facial features to form mask 12. As the deformable material cools and hardens, mask 12 solidifies and will retain its custom fitted shape. Before or after the deformable material solidifies into its final shape, custom fitted mask 12 is removed from the user's face and is ready for use, for example, in treating sleep disordered breathing. Although mask 12 is described primarily for use in treating breathing problems such as sleep disordered breathing, the present invention contemplates mask 12 being used or for any other suitable purpose for which a custom fitted mask may be used. As just one example, mask 12 may be used in delivering anesthesia during surgery or another medical procedure.

As described above, mask 12 is preferably formed and fitted to the user's face so as to conform substantially optimally to the user's unique bone structure and facial features, including at least a portion of the user's nose surrounding the user's nostrils. In one embodiment, mask 12 covers only the soft cartilaginous portions of the user's nose and portions of the user's face to the sides of and below the soft cartilaginous portions of the user's nose, but does not cover the hard bony portions of the user's nose generally above the soft cartilaginous portions of the user's nose. This may allow mask 12 to better conform to the unique shape of the user's face and, as a result of the improved fit, to provide reduced leakage, increased comfort, and better performance. In certain embodiments, mask 12 is substantially leak proof such that externally supplied gas is substantially prevented from escaping between first sheet 10 and the user's face. In the illustrated embodiment, mask 12 additionally covers the user's mouth to prevent leakage from the user's mouth. Such a mask 12 may be formed from a single sheet 10 of deformable material or may be formed from multiple sheets 10 of deformable material (e.g., a first covering the user's nose and a second covering the user's mouth) coupled to one another using one or more screws, clips, glue, the same or a different deformable material that is chemically bonded to sheets 10 of deformable material, or another appropriate fastening technique. Where multiple sheets of deformable material are used, the multiple sheets may be customized for the user at the same or at different times. For example, first sheet 10 may be customized to cover at least a portion of the user's nose at a first time and, if appropriate, a second sheet may be customized to cover the user's mouth at a subsequent second time and then coupled to first sheet 10.

In another embodiment, mask 12 covers at least a portion of the user's nose surrounding the user's nostrils (which may or may not be limited to the soft cartilaginous portions of the user's nose and portions of the user's face to the sides of and below the soft cartilaginous portions of the user's nose), covers the user's mouth, and additionally covers at least a portion of the user's face below the user's chin to better secure mask 12 to the user's face. Such a mask 12 may be formed from a single sheet 10 of deformable material or may be formed from multiple sheets 10 of deformable material (e.g., a first covering the user's nose and a second covering the user's mouth and chin or a first covering the user's nose, a second covering the user's mouth, and a third covering the user's chin) coupled to one another using one or more screws, clips, glue, the same or a different deformable material that is chemically bonded to the sheets of deformable material, or another appropriate fastening technique. Where multiple sheets 10 of deformable material are used, the multiple sheets 10 may be customized for the user at the same or at different times. For example, first sheet 10 may be customized to cover at least a portion of the user's nose at a first time and, if appropriate, a second sheet may be customized to cover the user's mouth and chin at a subsequent second time and then coupled to first sheet 10.

Figure 3:
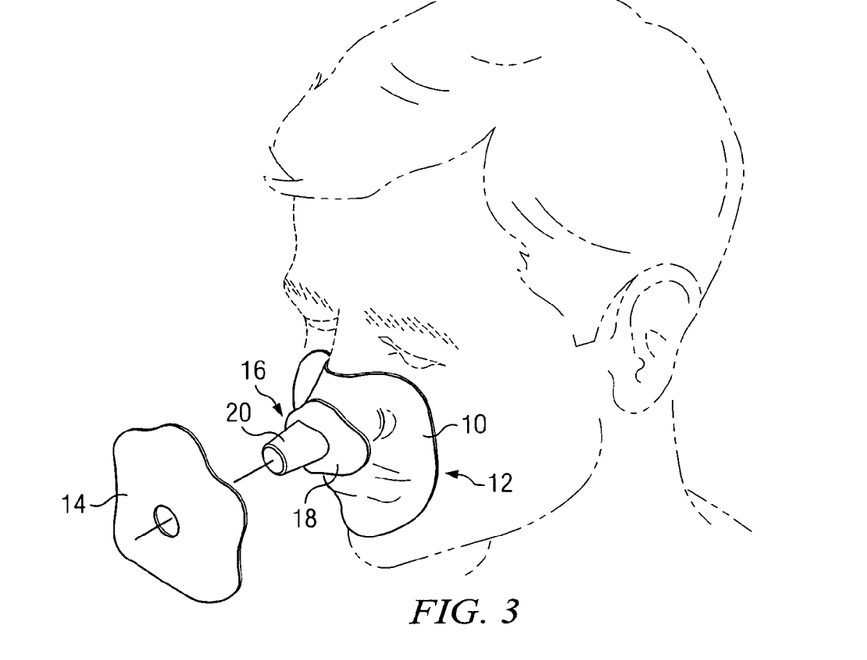
FIG. 3 illustrates an example second sheet of deformable material for configuring a custom fitted mask for coupling to an external gas supply system.

FIG. 3 illustrates a fitting 14 and an example second sheet 16 of deformable material for configuring mask 12 for coupling to an external gas supply system. Fitting 14 may be coupled to first sheet 10 when first sheet 10 is in a deformable state and is applied against the user's face if fitting 14 is not already coupled to first sheet 10. Coupling fitting 14 to first sheet 10 while first sheet 10 is in a deformable state may allow fitting 14 to chemically or otherwise bond to first sheet 10 to produce an integral unit.

Fitting 14 is adapted to couple mask 12 to an external gas supply system, for example, for use in treating sleep disordered breathing. Accordingly, fitting 14 may operate as a passage for delivering externally supplied gas to the user's nostrils. In one embodiment, fitting 14 includes a receiving portion 18 adapted to receive at least a portion of the first sheet 10 deformed about the user's nose. Fitting 14 may also include an extended portion 20 that is coupled to receiving portion 18. Second sheet 16 may be configured around at least extended portion 20 of fitting 14. In one embodiment, second sheet 16 may include a pre-formed hole configured to receive extended portion 20. Accordingly, second sheet 16 may be slid onto fitting 14 while fitting 14 and mask 12 are positioned on the user's face. Alternatively, second sheet 16 may include a thin sheet of deformable material that may be wrapped or otherwise configured around extended portion 20 of fitting 14 while fitting 14 and mask 12 are positioned on the user's face.

Similar to first sheet 10, second sheet 16 may include, for example, a suitable thermoplastic polymer and suitable fillers, stabilizers, coloring agents, antioxidants, antimicrobial agents, or other materials. As another example, second sheet 16 may include a light curing material such as the material sold under the name TRIAD by DENTSPLY INTERNATIONAL INC. In a more particular embodiment, second sheet 16 may include, possibly in addition to one or more other materials, one or more of the polycaprolactone polymers or other aliphatic polyesters that are described above with regard to FIG. 1 and first sheet 10.

In certain embodiments, second sheet 16 may include a thin sheet of deformable material that is already contoured in the shape of a portion of a generic fitting and a generic user's face, including at least the portion of the generic user's nose surrounding the generic user's nostrils. For example, second sheet 16 may be sized and shaped such that it will receive fitting 14 and overlap first sheet 10 over the soft cartilaginous portions of the generic user's nose and portions of the generic user's face to the sides of and below the soft cartilaginous portions of the generic user's nose. In certain other embodiments, second sheet 16 may include a thin sheet of deformable material that is substantially flat except for a depression sufficient to accommodate fitting 14 and a generic user's nose. In certain other embodiments, second sheet 16 may include a thin sheet of deformable material that is substantially flat over its entire surface and does not include any depressions.

Thin sheets of an appropriate deformable material may be obtained, for example, from CHESAPEAKE MEDICAL PRODUCTS, INC. Particularly where second sheet 16 is formed to include a depression for receiving fitting 14 and the user's nose, second sheet 16 may be formed using an injection molding process (i.e., deformable material is placed into an injection molding machine while in a liquid state), using a pressing process (i.e., deformable material is placed into a press while in a deformable state), or using any other suitable technique. Second sheet 16 may be sized for various classes of generic users, for example, large for men, medium for women, and small for children. In certain embodiments, many second sheets 16 may be mass produced quickly, inexpensively, and with high quality and uniformity. Second sheet 16 may include any other suitable features.

Figure 4:
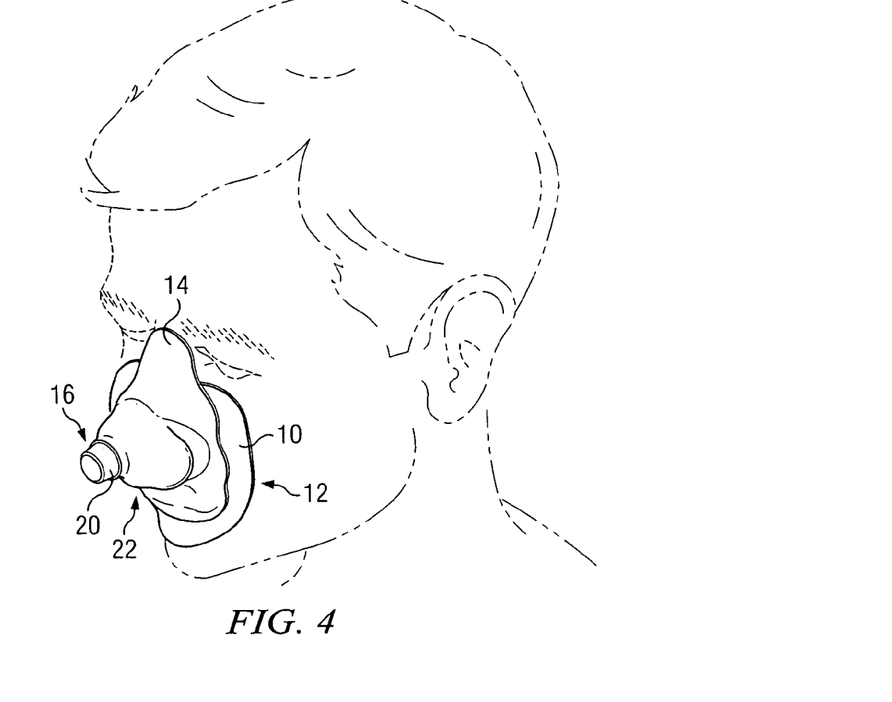
FIG. 4 illustrates an example second sheet of deformable material deformed against a fitting and a custom fitted or other mask to configure the mask for coupling to an external gas supply system.

FIG. 4 illustrates an example second sheet 16 of deformable material deformed against fitting 14 and underlying mask 12 to configure mask 12 for coupling to an external gas supply system. To form and fit second sheet 16 to a particular fitting 14 and user, second sheet 16 is placed in a deformable state. For example, where the deformable material of second sheet 16 includes one or more polycaprolactone polymers, second sheet 16 may be heated in a microwave oven, in water or other non-solvent neutral liquid, or in any other suitable manner to between approximately 140° F. and approximately 180° F. so as to place second sheet 16 in a deformable state. While in a deformable state, second sheet 16 is brought in contact with portions of fitting 14 and mask 12. A contact portion of second sheet 16 is applied against a contact portion of mask 12 such that fitting 14 is positioned between second sheet 16 and mask 12. Second sheet 16 is then pressed against or otherwise allowed to conform to the contours of fitting 14 and mask 12. Second sheet 16 may be pressed against or otherwise allowed to conform to fitting 14 and mask 12 while mask 12 is positioned on the user's face.

The pressing of second sheet 16 against fitting 14 and mask 12 may allow second sheet 16 to chemically or otherwise bond to fitting 14 and mask 12. Accordingly, second sheet 16, fitting 14, and mask 12 may become an integral unit as the deformable material of second sheet 16 cools and hardens. Whether or not providing an integral unit, mask 12, fitting 14, and second sheet 16 may be referred to as custom fitted mask 22. Before or after the deformable material of second sheet 16 solidifies into its final custom fitted shape, mask 22 may be removed from the user's face. Mask 22 is then ready for use, for example, in treating sleep disordered breathing. In certain embodiments, mask 22 is substantially leak proof such that externally supplied gas is substantially prevented from escaping between the contact portion of second sheet 16 and the contact portion of first sheet 10.

Although mask 22 is described as including a second sheet 14 that is deformed against an underlying custom fitted mask 12 to configure mask 12 for coupling to an external gas supply system, the present invention contemplates second sheet 16 being deformed against a non-custom fitted mask 12, with fitting 14 between second sheet 16 and mask 12, to configure mask 12 for coupling to an external gas supply system. For example, in certain embodiments, mask 12 may be a pre-fabricated generic mask. The present invention contemplates any suitable mask 12 being used to form mask 22.

Figure 5:
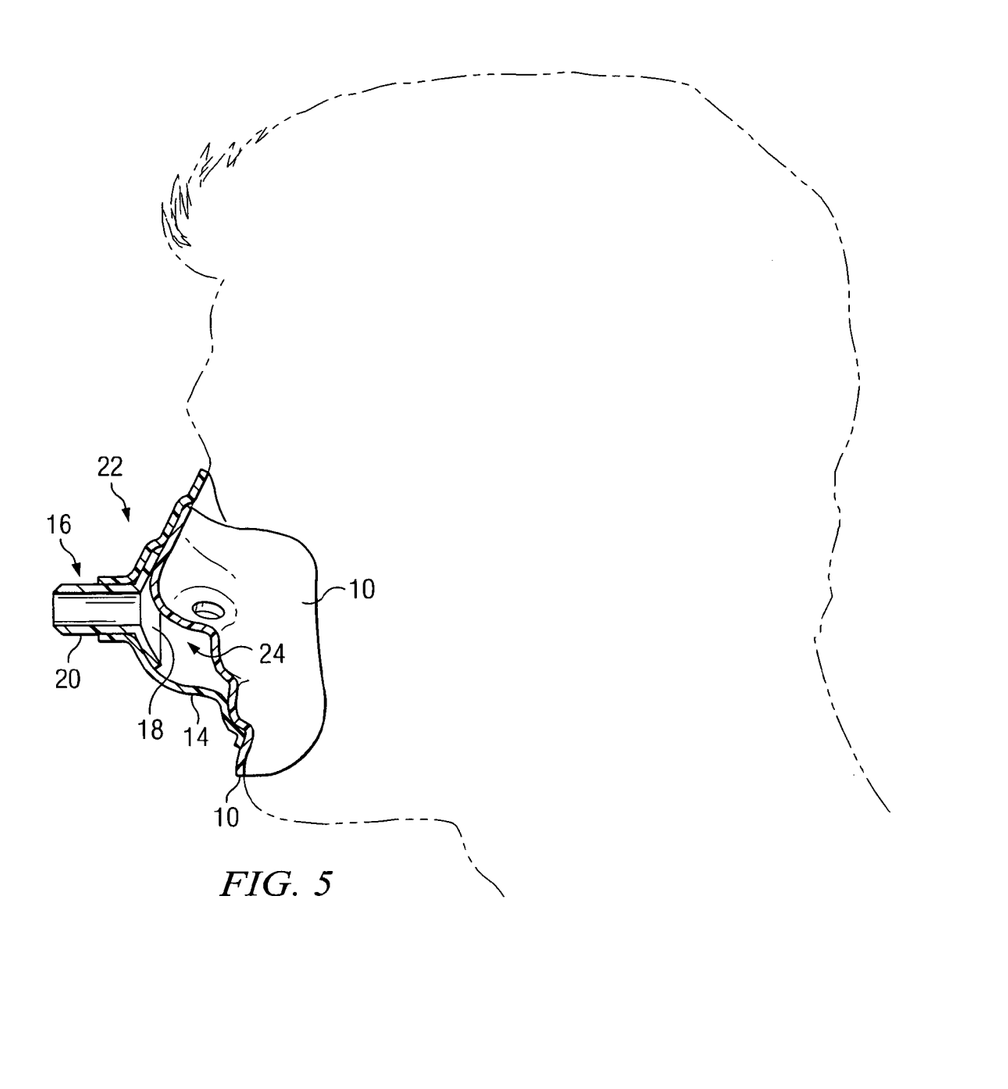
FIG. 5 illustrates a cross-section of an example custom fitted mask configured for coupling to an external gas supply system.

FIG. 5 illustrates a cross-section of an example custom fitted mask 22 configured for coupling to an external gas supply system. In certain embodiments, fitting 14 and second sheet 16 cooperate to form a void 24 that allows gas from an external gas supply system coupled to fitting 14 to flow to the user's nostrils.

Figure 6:
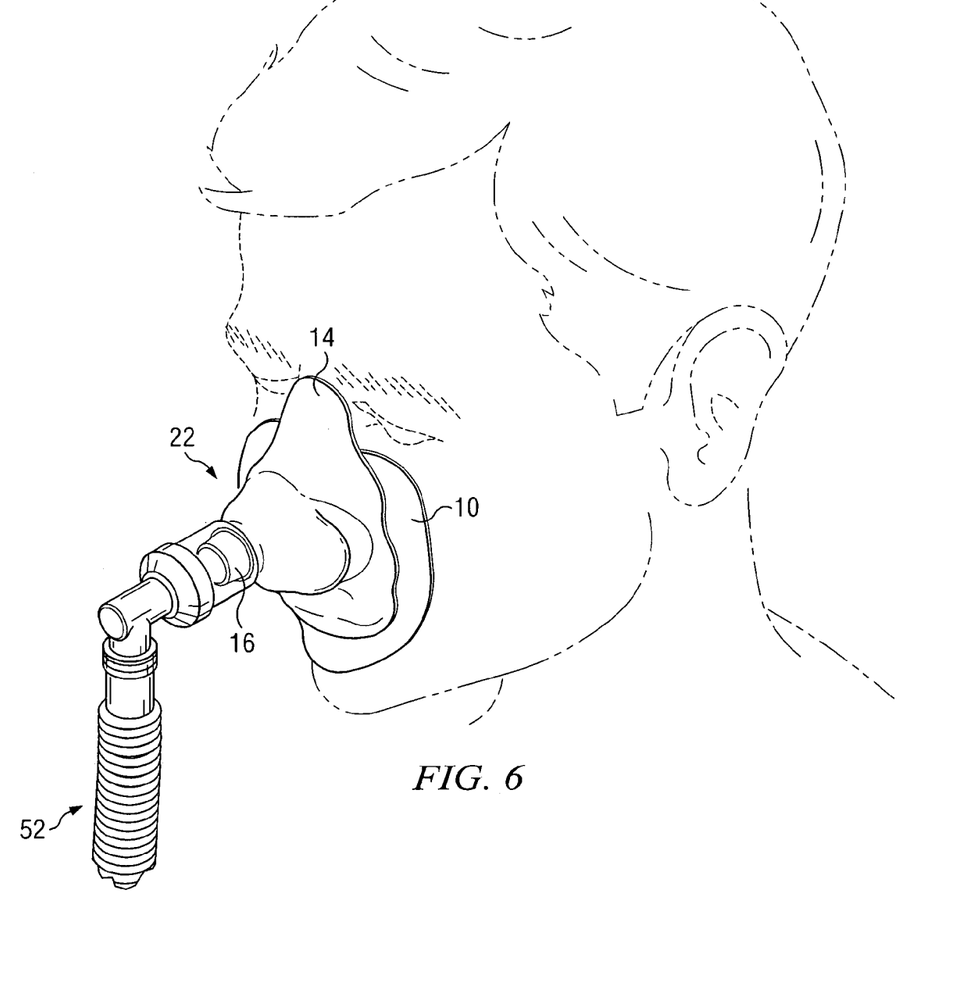
FIG. 6 illustrates an example custom fitted mask coupled to an external gas supply system.

FIG. 6 illustrates an example custom fitted mask 22 coupled to any suitable external gas supply system 52. For example, system 52 may be a continuous positive air pressure (CPAP) system for supplying air or another gas to the user's nose at positive pressure to help open the user's breathing passage and thereby improve the user's breathing. For example, system 52 may include a tube that snaps onto, is force fitted onto, or otherwise couples to fitting 16. Mask 22 may include buckles, snaps, or other devices to couple mask 22 to one or more straps, which may help secure mask 22 to the user's face during use. Although straps are described as an example, mask 22 may be secured in any appropriate manner.

Although the present invention has been described above in connection with several example embodiments, it should be understood that any number of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A method of forming a custom fitted mask configured for coupling to an external gas supply system, comprising:
   applying a first sheet of deformable material against a user's face surrounding the user's nostrils while the first sheet is in a deformable state;
   deforming the first sheet against the user's face to cause the first sheet to conform substantially optimally to the user's unique facial features;
   configuring a second sheet of deformable material around a fitting adapted for coupling to the external gas supply system;
   applying a contact portion of the second sheet against a contact portion of the first sheet while the second sheet is in a deformable state such that the fitting is positioned between the first and second sheets;
   deforming the contact portion of the second sheet against the contact portion of the first sheet with the fitting positioned between the first and second sheets to cause the contact portion of the second sheet to conform substantially optimally to the contact portion of the first sheet;
   allowing the contact portion of the second sheet to bond to the contact portion of the first sheet; and
   allowing the second sheet to transition from the deformable state to a non-deformable state to form the custom fitted mask configured for coupling to the external gas supply system.

2. The method of claim 1, wherein configuring the second sheet further comprises leaving a void between the first and second sheets for externally supplied gas to flow from the fitting to the user's nostrils.

3. The method of claim 1, wherein configuring the second sheet further comprises deforming the second sheet substantially optimally to the fitting.

4. The method of claim 3, wherein configuring the second sheet further comprises allowing the second sheet to bond to the fitting.

5. The method of claim 1, wherein deforming the second sheet further comprises conforming the second sheet substantially optimally to the fitting at substantially the same time that the contact portion of the second sheet conforms to the contact portion of the first sheet.

6. The method of claim 1, wherein configuring the second sheet around the fitting comprises inserting an extended portion of the fitting through a hole formed in the second sheet.

7. The method of claim 1, further comprising coupling an extended portion of the fitting to the external gas supply system.

8. The method of claim 1, wherein the custom fitted mask is substantially leak proof such that externally supplied gas is substantially prevented from escaping between the first sheet and the user's face and between the contact portion of the second sheet and the contact portion of the first sheet.

9. The method of claim 1, wherein before being applied to the user's face the first sheet is contoured in the shape of a portion of a generic user's face surrounding the generic user's nostrils.

10. The method of claim 1, wherein before being applied to the fitting the second sheet is substantially flat except for a depression sufficient to accommodate the fitting when the fitting is positioned between the first and second sheets.

11. The method of claim 1, wherein one or both of the first and second sheets comprises an injection molded blank.

12. The method of claim 1, further comprising transitioning the second sheet of deformable material from a non-deformable state to the deformable state, the second sheet of deformable material comprising a thermoplastic polymer that is heated to transition the second sheet to the deformable state.

13. The method of claim 12, wherein the thermoplastic polymer comprises a polycaprolactone polymer.

14. The method of claim 1, wherein the custom fitted mask comprises a mask for use in treating sleep disordered breathing.

15. A method of configuring a mask for coupling to an external gas supply system, comprising:
    configuring a sheet of deformable material around a fitting adapted for coupling to the external gas supply system;
    positioning a mask for configuration using the sheet, the mask comprising an interior surface configured to be directed toward and applied against a user's face and an exterior surface configured to be directed away from the user's face when the interior surface is applied against the user's face;
    a contact portion of the sheet against a contact portion of the exterior surface of the mask while the sheet is in a deformable state;
    deforming the contact portion of the sheet against the contact portion of the exterior surface of the mask with the fitting positioned between the sheet and the exterior surface of the mask to cause the contact portion of the sheet to conform substantially optimally to the contact portion of the exterior surface of the mask;
    allowing the contact portion of the sheet to bond to the contact portion of the exterior surface of the mask; and
    allowing the sheet to transition from the deformable state to a non-deformable state to form the custom fitted mask.

16. The method of claim 15, wherein configuring the sheet further comprises leaving a void between the sheet and the mask for externally supplied gas to flow from the fitting to the user's nostrils.

17. The method of claim 15, wherein configuring the sheet further comprises deforming the contact portion of the sheet substantially optimally to the contact portion of the fitting.

18. The method of claim 17, wherein configuring the sheet further comprises allowing the contact portion of the sheet to bond to the contact portion of the fitting.

19. The method of claim 15, wherein deforming the sheet further comprises conforming the sheet substantially optimally to the fitting at substantially the same time that the contact portion of the sheet conforms to the contact portion of the mask.

20. The method of claim 15, wherein configuring the sheet around the fitting comprises inserting an extended portion of the fitting through a hole formed in the sheet.

21. The method of claim 15, further comprising coupling an extended portion of the fitting to the external gas supply system.

22. The method of claim 15, wherein the custom fitted mask is substantially leak proof such that externally supplied gas is substantially prevented from escaping between the first sheet and the user's face and between the contact portion of the sheet and the contact portion of the mask.

23. The method of claim 15, wherein before being applied to the fitting the sheet is substantially flat except for a depression sufficient to accommodate the fitting when the fitting is positioned between the sheet and the mask.

24. The method of claim 15, wherein the sheet comprises an injection molded blank.

25. The method of claim 15, further comprising transitioning the sheet from a non-deformable state to the deformable state, the sheet of deformable material comprising a thermoplastic polymer that is heated to transition the sheet to the deformable state.

26. The method of claim 25, wherein the thermoplastic polymer comprises a polycaprolactone polymer.

27. The method of claim 15, wherein the mask comprises a mask for use in treating sleep disordered breathing.

28. A custom fitted mask configured for coupling to an external gas supply system, comprising:
    a first sheet of deformable material that has been deformed against a user's face surrounding the user's nostrils while the first sheet is in a deformable state to conform substantially optimally to the user's unique facial features;
    a fitting adapted for coupling to the external gas supply system; and
    a second sheet of deformable material configured around the fitting, the second sheet having been applied against the fitting while the second sheet is in a deformable state such that the fitting is positioned between the first and second sheets, a contact portion of the second sheet conforming substantially optimally to a contact portion of the first sheet and being bonded to the contact portion of the first sheet, the second sheet having been transitioned from the deformable state to a non-deformable state to form the custom fitted mask.

29. The custom fitted mask of claim 28, wherein the second sheet is configured around the fitting such that a void is left between the first and second sheets for externally supplied gas to flow from the fitting to the user's nostrils.

30. The custom fitted mask of claim 28, wherein the second sheet is deformed substantially optimally to the fitting.

31. The custom fitted mask of claim 30, wherein the second sheet is bonded to the fitting.

32. The custom fitted mask of claim 28, wherein the fitting comprises an extended portion inserted through a hole formed in the second sheet.

33. The custom fitted mask of claim 28, wherein the fitting comprises an extended portion for coupling to the external gas supply system.

34. The custom fitted mask of claim 28, wherein the custom fitted mask is substantially leak proof such that externally supplied gas is substantially prevented from escaping between the first sheet and the user's face and between the contact portion of the second sheet and the contact portion of the first sheet.

35. The custom fitted mask of claim 28, wherein before being applied to the user's face the first sheet is contoured in the shape of a portion of a generic user's face surrounding the generic user's nostrils.

36. The custom fitted mask of claim 28, wherein before being applied to the fitting the second sheet is substantially flat except for a depression sufficient to accommodate the fitting when the fitting is positioned between the first and second sheets.

37. The custom fitted mask of claim 28, wherein one or both of the first and second sheets comprises an injection molded blank.

38. The custom fitted mask of claim 28, wherein the second sheet of deformable material comprises a thermoplastic polymer.

39. The custom fitted mask of claim 38, wherein the thermoplastic polymer comprises a polycaprolactone polymer.

40. The custom fitted mask of claim 28, wherein the custom fitted mask comprises a mask for use in treating sleep disordered breathing.

41. A custom fitted mask configured for coupling to an external gas supply system, comprising:
   a mask adapted to be positioned on a user's face;
   a fitting adapted for coupling to the external gas supply system; and
   a sheet of deformable material that has been configured around the fitting, the sheet having been applied against the fitting while the sheet is in a deformable state such that the fitting is positioned between the exterior surface of the mask and the sheet, a contact portion of the sheet conforming substantially optimally to an exterior contact portion of the mask and being bonded to the exterior contact portion of the mask, the sheet having been transitioned from the deformable state to a non-deformable state to form the custom fitted mask.

42. The custom fitted mask of claim 41, wherein the sheet is configured around the fitting such that a void is left between the mask and the sheet for externally supplied gas to flow from the fitting to the user's nostrils.

43. The custom fitted mask of claim 41, wherein the sheet is deformed substantially optimally to the fitting.

44. The custom fitted mask of claim 43, wherein the sheet is bonded to the fitting.

45. The custom fitted mask of claim 41, wherein the fitting comprises an extended portion inserted through a hole formed in the sheet.

46. The custom fitted mask of claim 41, wherein the fitting comprises an extended portion for coupling to the external gas supply system.

47. The custom fitted mask of claim 41, wherein the custom fitted mask is substantially leak proof such that externally supplied gas is substantially prevented from escaping between the mask and the user's face and between the contact portion of the sheet and the contact portion of the mask.

48. The custom fitted mask of claim 41, wherein before being applied to the user's face the sheet is contoured in the shape of a first portion of a generic user's face surrounding the generic user's nostrils.

49. The custom fitted mask of claim 41, wherein before being applied to the fitting the sheet is substantially flat except for a depression sufficient to accommodate the fitting when the fitting is positioned between the mask and the sheet.

50. The custom fitted mask of claim 41, wherein one or both of the mask and the sheet comprises an injection molded blank.

51. The custom fitted mask of claim 41, wherein the sheet of deformable material comprises a thermoplastic polymer.

52. The custom fitted mask of claim 51, wherein the thermoplastic polymer comprises a polycaprolactone polymer.

53. The custom fitted mask of claim 41, wherein the mask comprises a mask for use in treating sleep disordered breathing.

* * * * *